United States Patent [19]
Mittendorf

[11] Patent Number: 5,877,343
[45] Date of Patent: Mar. 2, 1999

[54] EFFICIENT AND HIGHLY ENANTIOSELECTIVE PROCESS FOR THE PREPARATION OF ENANTIOMERICALLY PURE CYCLOPENTANE-β-AMINO ACIDS

[75] Inventor: Joachim Mittendorf, Wuppertal, Germany

[73] Assignee: Bayer Aktiengesellschaft, Leverkusen, Germany

[21] Appl. No.: 843,102

[22] Filed: Apr. 25, 1997

[30] Foreign Application Priority Data

May 3, 1996 [DE] Germany .................. 196 17 772.3

[51] Int. Cl.⁶ .................. C07C 261/00; C07C 69/74; C07C 229/00; C07C 61/06
[52] U.S. Cl. .................. 560/115; 560/122; 562/457; 562/504
[58] Field of Search .................. 562/504, 457; 560/122, 115

[56] References Cited

U.S. PATENT DOCUMENTS

| | | | |
|---|---|---|---|
| 3,560,565 | 2/1971 | Childress et al. | 260/556 |
| 5,037,809 | 8/1991 | Miyauchi et al. | 514/561 |

FOREIGN PATENT DOCUMENTS

| | | | |
|---|---|---|---|
| 0 571 870 A1 | 12/1993 | European Pat. Off. | |
| 44 00 749 A 1 | 7/1995 | Germany | C07C 229/48 |
| WO 95/19337 | 7/1995 | WIPO | |

OTHER PUBLICATIONS

Diphenylphosphonyl Azide. A New, Convienient Reagent for a Modified Curtius Reaction and for the Peptide Synthesis. J. An. Chem. Soc., 94:17, pp. 6203–6205, 1972 Yamada et al.

Database WPIDS on STN, DNC No. C90–108501, 'Cis–2–amino cyclopentane–carboxylic acid derivs.—used as antimicrobials for agricultural and horticultural use.' Abstract of JP 02174753, 1990.

J.Antibiot. (1991), 44(5), 546–549.

Chênevert et al., Tetrahedron: Asymmetry (1992), 3(2), 199–200.

Furuta et al., Tetrahedron Letters, (1987), 28(4) 5841–44.

*Primary Examiner*—Brian M. Burn
*Assistant Examiner*—Brian J. Davis
*Attorney, Agent, or Firm*—Sprung Kramer Schaefer & Briscoe

[57] ABSTRACT

The process according to the invention for the preparation of enantiomerically pure cyclopentane-β-amino acids of the general formula (I)

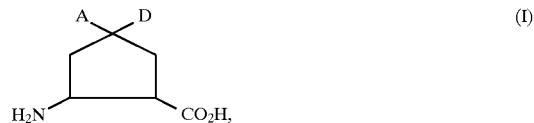

in which A and D have the meanings given in the description, is characterized in that meso-dicarboxylic acid anhydrides are first converted by asymmetric alcoholysis with allyl alcohols and in the presence of a chiral amine base present in enantiomerically pure form, in inert solvents, via the intermediate enantiomerically pure salt stage, into the enantiomerically pure dicarboxylic acid monoesters, in a further step these dicarboxylic acid monoesters are intermediately converted, in the sense of a Curtius rearrangement by reaction with azides, into the corresponding acid azides, and are subsequently converted into the corresponding rearranged isocyanates and the isocyanates are then reacted with allyl alcohols to give the compounds of the general formula (VII), and finally the cyclopentane-β-amino acids of the general formula (I) are obtained by splitting off the urethane and ester function.

18 Claims, No Drawings

EFFICIENT AND HIGHLY ENANTIOSELECTIVE PROCESS FOR THE PREPARATION OF ENANTIOMERICALLY PURE CYCLOPENTANE-β-AMINO ACIDS

The present invention relates to an efficient and highly enantioselective process for the preparation of enantiomerically pure cyclopentane-β-amino acids.

Cyclopentane-β-amino acids are known from the publications EP 571 870, JP 0 274 753 and J. Antibiot. (1991), 44 (5), 546–9. The publication WO 95/19337 describes a highly enantioselective process for the preparation of enantiomerically pure cyclopentane- and -pentene-β-amino acids. These are obtained starting from the corresponding meso-dicarboxylic acid anhydrides in six synthesic steps with overall yields of 28–40% of theory with an enantiomeric excess of ≧98%.

The invention relates to an efficient and highly enantioselective process for the preparation of enantiomerically pure cyclopentane-β-amino acids of the general formula (I)

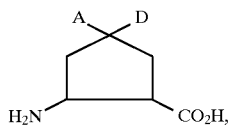

in which

A and D are identical or different and represent hydrogen, halogen or hydroxyl, or represent straight-chain or branched alkyl having up to 8 carbon atoms, which is optionally substituted once or twice in an identical or different manner by halogen, hydroxyl, phenyl, benzyloxy or carboxyl or by straight-chain or branched alkoxy, acyl or alkoxycarbonyl having in each case up to 6 carbon atoms or by a group of the formula —NR$^7$R$^8$, wherein R$^7$ and R$^8$ are identical or different and denote hydrogen, phenyl or straight-chain or branched alkyl having up to 6 carbon atoms, or A and D together represent a radical of the formula

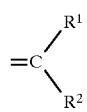

wherein

R$^1$ and R$^2$ are identical or different and denote hydrogen, halogen or straight-chain or branched alky, alkoxy or hydroxyacyl having up to 8 carbon atoms, benzyl or phenyl, which is characterized in that meso-dicarboxylic acid anhydrides of the general formula (II)

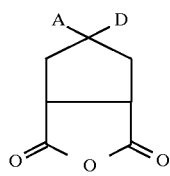

in which

A and D have the abovementioned meanings, are first converted by an asymmetric alcoholysis with allyl alcohols of the general formula (III)

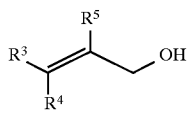

in which

R$^3$, R$^4$ and R$^5$ are identical or different and represent hydrogen, or represent straight-chain or branched alkyl having up to 5 carbon atoms, or represent phenyl, which is optionally substituted up to 3 times in an identical or different manner by halogen, cyano, trifluoromethoxy, nitro or trifluoromethyl or by straight-chain or branched alkyl or alkoxy having in each case up to 6 carbon atoms, or R$^3$ represents a 5- to 7-membered aromatic heterocyclic radical having up to 3 heteroatoms from the series consisting of S, N and/or O, and in the presence of equimolar amounts of a chiral amine base present in enantiomerically pure form, in inert solvents, via the intermediate enantiomerically pure salt stage of the general formula (IV)

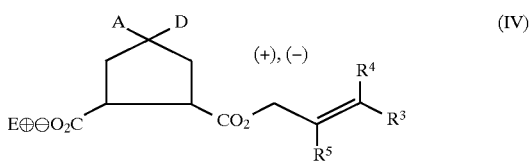

in which

A, D, R$^3$, R$^4$ and R$^5$ have the abovementioned meanings and

E represents the chiral amine base, into the enantiomerically pure compounds of the general formula (IVa)

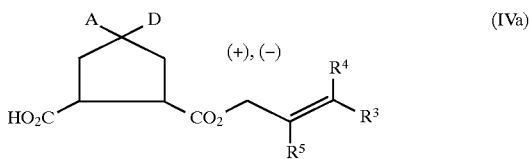

in which

A, D, R$^3$, R$^4$ and R$^5$ have the abovementioned meanings, in a further step are intermediately converted, in the sense of a Curtius rearrangement by reaction of the compounds of the general formula (IVa) with azides of the general formula (V)

in which

R$^6$ represents phenyl, or represents straight-chain or branched alkyl having up to 6 carbon atoms, in inert solvents and in the presence of a base, or by activation of the carboxyl group of the compounds of the general formula (IVa) and subsequent reaction with alkali metal azides or trialkylsilyl azides, into the corresponding acid azides, and are subsequently converted into the corresponding rearranged isocyanates of the general formula (VI)

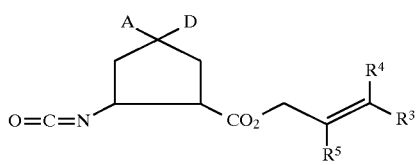

wherein

A, D, $R^3$, $R^4$ and $R^5$ have the abovementioned meanings, and the isocyanates are then reacted with compounds of the general formula (III) to give the compounds of the general formula (VII)

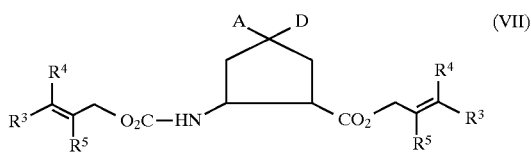

in which $R^3$, $R^4$, $R^5$, A and D have the abovementioned meanings, and finally the urethane and the ester function are split in inert solvents and in the presence of a Pd catalyst and/or a phosphine and a nucleophilic auxiliary.

The process according to the invention can be illustrated by way of example by the following equation:

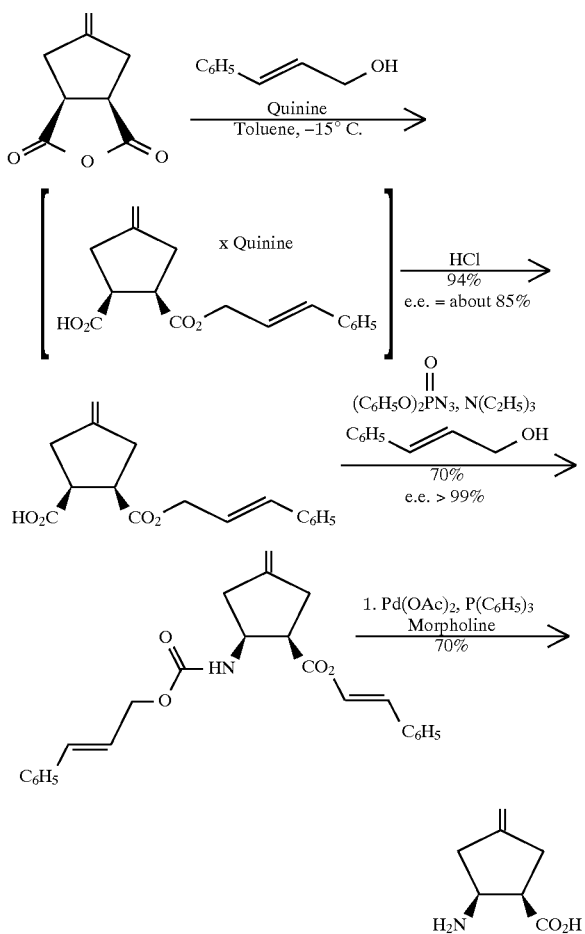

A heterocyclic radical in the context of the invention in general represents an aromatic 5- to 7-membered, preferably 5- to 6-membered heterocyclic radical, which can contain up to 3 heteroatoms from the series consisting of S, N and/or O. Examples which may be mentioned are: pyridyl, thienyl, furyl, pyrrolyl, thiazolyl, oxazolyl or imidazolyl. Pyridyl and thienyl are preferred.

Surprisingly, the chiral compounds of the general formula (I) are obtained in an elegant manner with a very high enantiomeric purity and simultaneously very high yields by carrying out the process according to the invention.

In contrast to the abovementioned prior art, the process according to the invention renders possible a highly enantioselective route for synthesis of enantiomerically pure cyclopentane-β-amino acids in a synthesis sequence shortened from 6 to 3 stages with an overall yield of ≧45% of theory and an enantiomeric excess of ≧99% starting from the corresponding meso-dicarboxylic acid anhydride via a Curtius rearrangement.

Another advantage of the process according to the invention is that the volume yield of the synthesis of the dicarboxylic acid monoesters (formula IVa) is considerably higher compared with the process of WO 95/19337. Furthermore, the intermediate isolation of the compounds of the general formula (IV) is omitted. Although the compounds of the general formula (IVa) are obtained only with an enantiomeric excess of 80–>97%, in the next stage (Curtius rearrangement) a concentration to an enantiomeric excess of >99% takes place during crystallization of the compounds of the general formula (VI).

In contrast to the prior art, the process according to the invention is also distinguished by the fact that the Hofmann rearrangement and the introduction and splitting off of a protective group is replaced by an efficient Curtius rearrangement.

The splitting off of the urethane and ester function of the compounds of the general formula (VII) furthermore takes place in one step; the product crystallizes out of the reaction mixture and, in contrast to the prior art, can be isolated simply by filtration.

Another advantage of the process according to the invention is that, in contrast to the compounds of the formula (V) of WO 95/19337, the compounds of the general formula (VII) are crystalline and as a rule crystallize out of the reaction mixture. This allows easier handling and, by crystallization, an enrichment of the enantiomer purity to be achieved.

Possible solvents for the reaction of the dicarboxylic acid anhydrides of the general formula (II) are all the inert organic solvents which do not change under the reaction conditions. These include, preferably, ethers, such as diethyl ether, dioxane, diisopropyl ether, tert-butyl methyl ether, tetrahydrofuran or glycol dimethyl ether, or hydrocarbons, such as toluene, benzene, xylene, hexane, cyclohexane or petroleum fractions, or chlorinated hydrocarbons, such as chloroform or methylene chloride, or amides, such as dimethylformamide, dimethylacetamide or hexamethylphosphoric acid triamide, or glacial acetic acid, dimethyl sulphoxide, acetonitrile or pyridine. Diisopropyl ether, diethyl ether, dioxane, tert-butyl methyl ether and toluene are preferred for the individual steps.

The reaction temperatures can be varied within a relatively wide range. In general, the reaction is carried out between −60° C. and +40° C., preferably between −20° C. and +25° C.

The reactions can be carried out under normal pressure, but also under increased or reduced pressure (for example 0.5 to 80 bar). The reactions are in general carried out under normal pressure.

Suitable alcohols for the alcoholysis and for the reaction in the sense of a Curtius rearrangement (formula III) are primary allyl alcohols, such as, for example, allyl or cinnamyl alcohol. Trans-cinnamyl alcohol is particularly preferred.

Suitable chiral amine bases for the process according to the invention are preferably alkaloids and cinchona alkaloids. Cinchona alkaloids, such as, for example, (+),(-)-quinine, (+),(-)-hydroquinine, (+),(-)-cinchonidine, (+),(-)-epiquinidine, (+),(-)-epicinchonidine, (+),(-)-cinchonine, (+),(-)-epicinchonine, (+),(-)-epiquinine, (+),(-)-hydroquinidine, (+),(-)-4-chlorobenzoate-epiquinine or (+),(-)-4-chlorobenzoate-epicinchonine. (+),(-)-Quinine and (+),(-)-quinidine are particularly preferred.

The chiral amine base is employed in equivalent amounts per mole of the dicarboxylic acid anhydrides of the general formula (II).

Suitable acids for the recovery of the free chiral amine base are, for example, mineral acids, such as hydrochloric acid, hydrobromic acid or sulphuric acid.

The acid is in general employed in an amount of 1 mol to 10 mol, preferably 1.5 mol to 4 mol, per mole of the compounds of the general formula (IV).

The recovery is in general carried out in a temperature range from 0° C. to +50° C. preferably from 20° C. to 30° C., under normal pressure.

The Curtius rearrangement is in general carried out in one of the abovementioned inert solvents. Preferred solvents are cyclic hydrocarbons, such as benzene, toluene or xylene, or ethers, such as dioxane or tetrahydrofuran. Toluene is preferred.

Suitable amines for the Curtius rearrangement are organic amines, such as N-ethylmorpholine, N-methylmorpholine, pyridine, triethylamine or N-methylpiperidine. Triethylamine is preferred.

The base is in general employed in an amount of 1 mol to 3 mol, preferably 1 mol to 1.5 mol, per mole of the compounds of the general formula (IVa).

Suitable azides of the formula (V) for the Curtius rearrangement are phosphoric acid ester-azides, such as phosphoric acid diphenyl ester-azide or phosphoric acid diethyl ester-azide. Phosphoric acid diphenyl ester-azide is preferred.

It is also possible first to convert the carboxylic acid into the corresponding activated derivatives with activating reagents, such as $C_1$–$C_4$-alkyl chloroformates in the presence of an amine, thionyl chloride, phosphorus pentachloride or phosphorus oxychloride, and then to prepare the carboxylic acid azides by reaction with alkali metal azides, such as sodium azide, or trialkylsilyl azides, such as trimethylsilyl azide.

The Curtius rearrangement is in general carried out in a temperature range from 0° C. to +130° C., preferably from 60° C. to 110° C.

The Curtius rearrangement is in general carried out under normal pressure. However, it is also possible to carry out the process under reduced pressure or under increased pressure (for example in a range from 0.5 to 5 bar).

The activation of the carboxyl group of the compounds of the general formula (IVa) is usually carried out with ethyl chloroformate/triethylamine, and in general in a temperature range from –30° to +25° C.

The acid azides obtained in such a manner are subsequently converted into the corresponding isocyanates of the general formula (VI) by heating a solution in one of the abovementioned inert solvents to temperatures of 60° C. to 120° C.

The isocyanates of the formula (VI) can be isolated, or after their preparation are reacted with the alcohols of the general formula (III).

The urethane and ester function in the compounds of the general formula (VII) are in general split off in one of the abovementioned inert solvents. Preferred solvents are hydrocarbons, such as toluene, benzene or xylene, ethers, such as tetrahydrofuran or diethyl ether, esters, such as ethyl acetate, alcohols, such as ethanol, methanol or isopropanol, acetonitrile or dimethylformamide. Acetonitrile, dimethylformamide, ethyl acetate or ethanol are particularly preferred.

The splitting off is in general carried out in a temperature range from 0° C. to +100° C., preferably at 20° C. to 80° C.

The splitting off is in general carried out under normal pressure. However, it is also possible to carry out the process under reduced pressure or under increased pressure (for example in a range from 0.5 to 5 bar).

Suitable nucleophilic auxiliaries for the splitting off are, for example, carboxylic acids and alkali metal salts thereof (for example formic acid, acetic acid, 2-ethylhexanoic acid and sodium 2-ethyl-hexanoate), organic amines, such as morpholine, triethylamine, pyrrolidine, dimethyltrimethylsilylamine, trimethylsilylmorpholine and n-butylamine, dimedone, sodium diethylmalonate, tributyltin hydride, N,N-dimethylbarbituric acid or ammonium formate. Morpholine is preferred.

The auxiliary is in general employed in an amount of 1 mol to 20 mol, preferably 1.1 mol to 3 mol, per mole of the compounds of the general formula (VII).

Suitable Pd catalysts in the context of the process according to the invention are, for example, tetrakistriphenylphosphinepalladium(0) $(Pd(PPh_3)_4)$, palladium dibenzylidene acetone $(Pd_2(dba)_3)$, $Pd_2(dba)_3 \times CHCl_3$, $Pd(dba)_2$, $PdCl_2$, $Pd(OAc)_2$, $PdCl_2(PhCN)_2$, $PdCl_2(CHl_3CN)_2$ or $PdCl_2(PPh_3)_2$. Palladium(II) actetate $(Pd(OAc)_2)$ is preferred.

The catalyst is in general employed in an amount of 0.0001 mol to 0.2 mol, preferably 0.001 mol to 0.05 mol, per mole of the compounds of the general formula (VII).

Suitable phosphines are in general $C_1$–$C_4$-trialkyl- and triarylphosphines, such as triphenylphosphine, triisopropylphosphine or tri-o-tolylphosphine. Triphenyl-phosphine is preferred.

The compounds of the general formula (II) are known per se or can be prepared by published methods.

The alcohols of the general formula (III), (IIIa) and (V) are known.

The compounds of the general formula (VII) are new and can be prepared as described above.

Compounds which are preferably prepared by the process according to the invention are enantiomerically pure compounds of the general formula (I)
in which
  A and D are identical or different and represent hydrogen or fluorine, or represent straight-chain or branched alkyl having up to 6 carbon atoms, or
  A and D together represent a radical of the formula $$=C{\overset{\displaystyle R^1}{\underset{\displaystyle R^2}{\diagup\!\!\!\diagdown}}}$$

wherein
    $R^1$ and $R^2$ are identical or different and denote hydrogen, fluorine, bromine or straight-chain or branched alkyl having up to 6 carbon atoms, benzyl or phenyl.

Compounds which are particularly preferably prepared by the process according to the invention are enantiomerically pure compounds of the general formula (I)

in which

A and D are identical or different and represent hydrogen, or represent straight-chain or branched alkyl having up to 4 carbon atoms, or A and D together represent a radical of the formula

wherein

R¹ and R² are identical or different and denote hydrogen or straight-chain or branched alkyl having up to 4 carbon atoms.

The process according to the invention allows access to enantiomerically pure cyclopentane-β-amino acids of the general formula (I), which are valuable medicaments having an antimycotic and antibacterial activity, in an efficient, elegant and highly enantioselective manner and at the same time with a high yield.

PREPARATION EXAMPLES

Example 1

1-(E)-Cinnamyl (1R,2S)-4-methylenecyclopentane-1,2-dicarboxylate

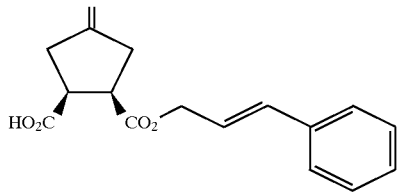

4-Methylene-1,2-cyclopentane-dicarboxylic acid anhydride (90.0 g, 591 mmol) is dissolved in toluene (2400 ml) under an $N_2$ atmosphere. Quinine (191.7 g, 591 mmol) and then trans-cinnamyl alcohol (119.2 g, 888 mmol) are added at $-15°$ C. The reaction mixture is stirred at $-15°$ C. for at least 4 hours. It is allowed to warm to room temperature and washed with 1N HCl (3×900 ml) and water (2×900 ml). The product is then extracted from the organic phase with 2% strength aqueous $K_2CO_3$ solution (1×4.5 l, 2×1.5 l). The combined aqueous phases are washed with ethyl acetate (2×1 l), covered with a layer of toluene (600 ml) and adjusted to pH 2 with 10% hydrochloric acid, while stirring vigorously. After separation of the phases, the product is extracted twice more with toluene (2×600 ml). The combined toluene phases are washed with water (2×400 ml) and concentrated in vacuo at $50°$ C./about 20 mbar.

Yield: 159.1 g, 94% of theory Enantiomeric excess e.e.≧85% (HPLC, Chiracel, OD-H, eluent: n-heptane/isopropanol).

If toluene (180 ml) is then added to the product and the suspension formed is stirred for about 1 hour, filtration and evaporation of the filtrate in vacuo gives 1-(E)-cinnamyl (1R,2S)-4-methylenecyclopentane-1,2-dicarboxylate (144.6 g, 85% of theory) with an enantiomeric excess of e.e.≧98% (HPLC, Chiracel OD-H, eluent: n-heptane/isopropanol).

$C_{17}H_{18}O_4$ (286.3); theory: C 71.31% H 6.34%; found: C 71.27% H 6.42%

Example 1a 1-(E)-Cinnamyl (1S,2R)-4-methylenecyclopentane-1,2-dicarboxylate

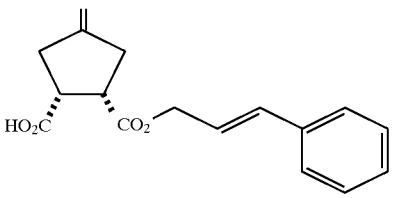

A suspension of quinidine (179.4 g, 553 mmol) is cooled to $-15°$ C. under an $N_2$ atmosphere, and 4-methylenecyclopentane-1,2-dicarboxylic acid anhydride (84.0 g, 553 mmol) and trans-cinnamyl alcohol (111.2 g, 829 mmol) are added. The reaction mixture is stirred at $-15°$ C. for at least 4 hours. Working up is carried out analogously to the preparation of the compound from Example 1.

Yield: 147.3 g, 93% of theory Enantiomeric excess e.e.≧93% (HPLC, Chiracel, OD-H, eluent: n-heptane/isopropanol).

$C_{17}H_{18}O_4$ (286.3); theory: C 71.31% H 6.34%; found: C 71.23% H 6.32%

Example 2

(E)-Cinnamyl (1R,2S)-2-N-((E)-cinnamyloxycarbonyl)amino-4-methylene-1-cyclopentane-carboxylate

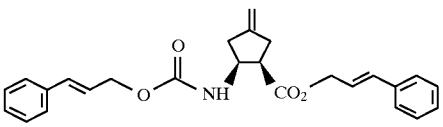

Triethylamine (3.5 g, 34.7 mmol) and phosphoric acid diphenyl ester-azide (9.6 g, 34.9 mmol) are successively added dropwise to a solution of the compound from Example 1 (10.0 g, 34.9 mmol, e.e.≧85%) in toluene (70 ml) under a nitrogen atmosphere.

The reaction mixture is heated to $90°$ C. for about 30 minutes, until no further nitrogen escapes. Trans-cinnamyl alcohol (5.6 g, 41.9 mmol) is then added dropwise at $90°$ C. and the mixture is heated under reflux under nitrogen overnight. The reaction mixture is allowed to cool to room temperature, while stirring, and is cooled further down to about $3°$ C. with an ice-bath, the product which has precipitated out is filtered off with suction and washed with a total of 50 ml of cold toluene, and the product is dried in vacuo at $50°$ C.

Yield: 10.3 g, 70% of theory, white crystals Enantiomeric excess e.e.≧99% (HPLC, Chiracel, OD-H, eluent: n-heptane/isopropanol +trifluoroacetic acid).

Melting point: $136°$ C.; $C_{26}H_{27}NO_4$ (417.51); theory: C 74.80% H 6.52% N 3.36%; found: C 74.88% H 6.44% N 3.51%

If the reaction described above is carried out with the compound from Example 1 with an enantiomeric excess of e.e.≧98% under otherwise analogous conditions, the product is obtained in a yield of 11.7 g (80% of theory) with an enantiomeric excess of≧99%.

Example 2a
(E)-Cinnamyl (1S,2R)-2-N-((E)-cinnamyloxycarbonyl) amino-4-methylene-1-cyclopentane-carboxylate

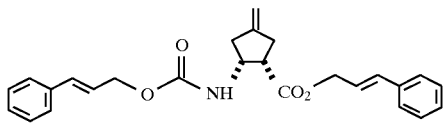

The preparation is achieved analogously to the preparation of the compound from Example 2 starting from the compound from Example 1a (30.0 g, 104.8 mmol).

Yield: 34.6 g, 79.1% of theory, Enantiomeric excess e.e.≧99% (HPLC, Chiracel OD-H, eluent: n-heptane/ isopropanol+trifluoroacetic acid).

Melting point: 137° C.; $C_{26}H_{27}NO_4$ (417.51); theory: C 74.80% H 6.52% N 3.36%; found: C 74.99% H 6.63% N 3.34%

Example 3
Allyl (1R,2S)-2-N-((E)-cinnamyloxycarbonyl)-amino-4-methylene-1-cyclopentane-carboxylate

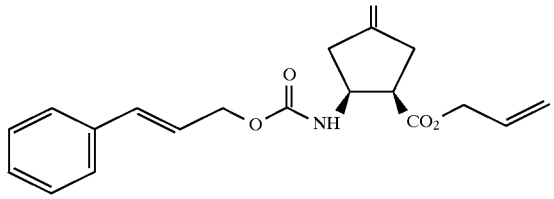

The preparation is carried out analogously to that described for Example 2, starting from 1-allyl (1R,2S)-4-methylene-cyclopentane-1,2-dicarboxylate (DE 44 007 49 A1; 7.3 g, 34.9 mmol, e.e.≧96%).

Yield: 7.9 g, 66% of theory, white crystals; $C_{20}H_{23}NO_4$ (341.38); theory: C 70.36% H 6.79% N 4.10%; found: C 70.25% H 6.97% N 4.08%

Example 4
(−)-(1R,2S)-2-Amino-4-methylene-cyclopentane-1-carboxylic acid

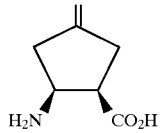

Triphenylphosphine (5.38 g, 20.5 mmol), morpholine (75.1 g, 862 mmol) and palladium(II) acetate (0.97 g, 4.3 mmol) are added successively to a solution of the compound from Example 2 (180.0 g, 431 mmol) in ethyl acetate (1500 ml) under an $N_2$ atmosphere. The reaction mixture is heated under reflux for 2 hours and then cooled to about 60° C. The product which has precipitated out is filtered off with suction, washed with ethyl acetate and dried in vacuo. The crude product is recrystallized twice from 85% aqueous ethanol.

Yield: 42.6 g, 70% of theory, white crystals; Melting point: 222° C.; $[\alpha]_D^{20}=-31.6$ (c=1, $H_2O$); $C_7H_{11}NO_2$ (141.2); theory: C 59.56% H 7.85% N 9.92%; found: C 59.46% H 7.85% N 9.88%

The preparation of the compound from Example 4 is achieved analogously and in almost the same yield starting from the compound from Example 3.

Example 4a
(+)-(1S,2R)-2-Amino-4-methylene-cyclopentane-1-carboxylic acid

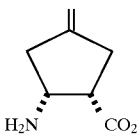

The preparation is achieved analogously to the preparation of the compound from Example 4 starting from the compound from Example 2a (60.3 g, 144.4 mmol).

Yield: 12.4 g, 67.6% of theory; Melting point: 233° C. (decomposition); $[\alpha]_D^{20}=+32.2$ (c=1.02, $H_2O$); theory: C 59.56% H 7.85% N 9.92%, found: C 59.09% H 7.74% N 9.87%

Example 5
1-(E)-Cinnamyl (1R,2S)-cyclopentane-1,2-dicarboxylate

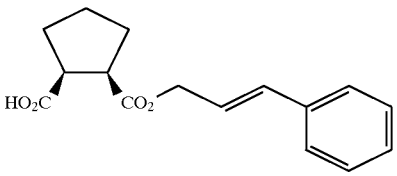

Cyclopentane-1,2-dicarboxylic acid anhydride (22.0 g, 157.1 mmol) and transcinnamyl alcohol (31.6 g, 235.7 mmol) are added successively to a suspension of quinine (50.9 g, 157.1 mmol) in toluene (634 ml) under an $N_2$ atmosphere at −15° C. The reaction mixture is stirred at −15° C. for at least 4 hours. It is allowed to warm to room temperature and is washed with 1N HCl (2×240 ml) and water (240 ml). The product is then extracted from the organic phase with 2.2% aqueous $K_2CO_3$ solution (1×1210 ml, 1×400 ml). The combined aqueous phases are washed with ethyl acetate (2×260 ml), covered with a layer of toluene (260 ml) and adjusted to pH 2 with 10% hydrochloric acid, while stirring vigorously. After separation of the phases, the product is extracted once more with toluene (260 ml). The combined toluene phases are washed with water (2×130 ml) and concentrated in vacuo at 50° C.

Yield: 40.2 g (93% of theory); Enantiomeric excess e.e.≧86% (HPLC); $C_{16}H_{18}O_4$ (274.3); theory: C 70.06% H 6.61%; found: C 69.66% H 6.42%

Example 6
(E)-Cinnamyl (1R,2S)-2-N-((E)-cinnamyloxycarbonyl) amino-cyclopentane-1-carboxylate

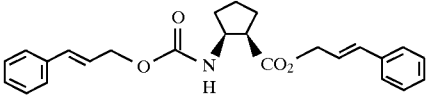

Triethylamine (14.3 g, 142 mmol) and phosphoric acid diphenyl ester-azide (39.4 g, 143 mmol) are successively added dropwise to a solution of the compound from Example 5 (39.3 g, 143 mmol) in toluene (286 ml) under an $N_2$ atmosphere.

The reaction mixture is heated to 90° C. for 30 minutes, trans-cinnamyl alcohol (23.0 g, 172 mmol) is then added dropwise at this temperature and the mixture is heated under reflux overnight. It is allowed to cool to 30° C., while stirring. and the crude product (14.2 g) which has precipitated out is filtered off with suction and rinsed with cold toluene (60 ml). The mother liquor is washed successively with 5% aqueous citric acid solution (410 ml), water (410 ml), saturated NaHCO$_3$ solution (410 ml) and saturated NaCl solution (410 ml). After the organic phase has been concentrated in vacuo, further crude product (30.0 g) is obtained. The crude product is then recrystallized from isopropanol.

Yield: 33.3 g (57.3% of theory), white crystals; Enantiomeric excess e.e.≧99% (BPLC, Chiracel OD-H); Melting point: 84°–85° C.; C$_{25}$H$_{27}$NO$_4$ (405.5); theory: C 74.05% H 6.71% N 3.45%; found: C 74.12% H 6.58% N 3.53%

Example 7

(−)-(1R,2S)-2-Amino-cyclopentane-1-carboxylic acid

Morpholine (19.3 g, 221 mmol) and palladium(II) acetate (0.062 g. 0.28 mmol) are added to a solution of the compound from Example 6 (44.8 g, 110.5 mmol) and triphenylphosphine (1.37 g, 5.2 mmol) in ethanol (127 ml) under an N$_2$ atmosphere. The reaction mixture is heated under reflux for 2 hours, 3-mercapto-1,2,4-triazole (1.12 g, 11.1 mmol) is added and the mixture is heated under reflux for a further 1.5 hours and then cooled to 0°–5° C. The crude product which has precipitated out is filtered off with suction, washed with ethanol and dried in vacuo. The crude product is recrystallized from 85% aqueous ethanol in the presence of 5 mol% of mercapto-1,2,4-triazole.

Yield: 9.4 g (66% of theory), white crystals; Melting point: 218° C. (decomposition); $[\alpha]_D^{20}$=9.9 (c=1.0, H$_2$O); C$_6$H$_{11}$NO$_2$ (129.2); theory: C 55.80% H 8.59% N 10.84%; found: C 55.53% H 8.24% N 10.83%

I claim:

1. Process for the preparation of enantiomerically pure cyclopentane-β-amino acids of the general formula (I)

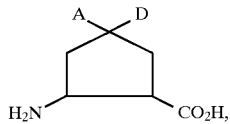

in which

A and D are identical or different and represent hydrogen, halogen or hydroxyl, or represent straight-chain or branched alkyl having up to 8 carbon atoms, which is optionally substituted once or twice in an identical or different manner by halogen, hydroxyl, phenyl, benzyloxy or carboxyl or by straight-chain or branched alkoxy, acyl or alkoxycarbonyl having in each case up to 6 carbon atoms or by a group of the formula —NR$^7$R$^8$, wherein R$^7$ and R$^8$ are identical or different and denote hydrogen, phenyl or straight-chain or branched alkyl having up to 6 carbon atoms, or A and D together represent a radical of the formula

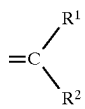

wherein

R$^1$ and R$^2$ are identical or different and denote hydrogen, halogen or straight-chain or branched alkyl, alkoxy or hydroxyacyl having up to 8 carbon atoms, benzyl or phenyl, characterized in that meso-dicarboxylic acid anhydrides of the general formula (II)

in which

A and D have the abovementioned meanings, are first converted by an asymmetric alcoholysis with allyl alcohols of the general formula (III)

in which

R$^3$, R$^4$ and R$^5$ are identical or different and represent hydrogen, or represent straight-chain or branched alkyl having up to 5 carbon atoms, or represent phenyl, which is optionally substituted up to 3 times in an identical or different manner by halogen, cyano, trifluoromethoxy, nitro or trifluoromethyl or by straight-chain or branched alkyl or alkoxy having in each case up to 6 carbon atoms, or R$^3$ represents a 5- to 7-membered aromatic heterocyclic radical having up to 3 heteroatoms from the series consisting of S, N and/or O, and in the presence of equimolar amounts of a chiral amine base present in enantiomerically pure form, in inert solvents, via the intermediate enantiomerically pure salt stage of the general formula (IV)

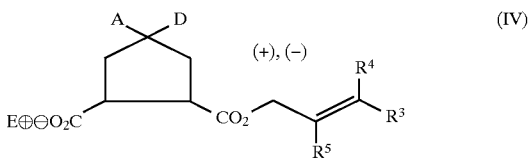

in which

A, D, R$^3$, R$^4$ and R$^5$ have the abovementioned meanings and

E represents the chiral amine base, into the enantiomerically pure compounds of the general formula (IVa)

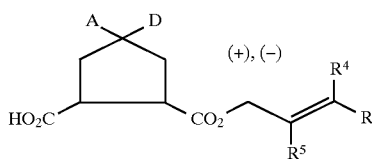

in which

A, D, $R^3$, $R^4$ and $R^5$ have the abovementioned meanings, in a further step are intermediately converted, in the sense of a Curtius rearrangement by reaction of the compounds of the general formula (IVa) with azides of the general formula (V)

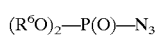

in which $R^6$ represents phenyl, or represents straight-chain or branched alkyl having up to 6 carbon atoms, in inert solvents and in the presence of a base, or by activation of the carboxyl group of the compounds of the general formula (IVa) and subsequent reaction with alkali metal azides or trialkylsilyl azides, into the corresponding acid azides, and are subsequently converted into the corresponding rearranged isocyanates of the general formula (VI)

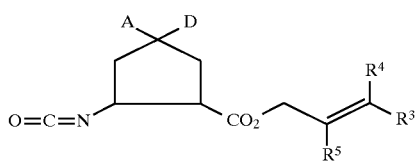

wherein

A, D, $R^3$, $R^4$ and $R^5$ have the abovementioned meanings, and the isocyanates are then reacted with compounds of the general formula (III) to give the compounds of the general formula (VII)

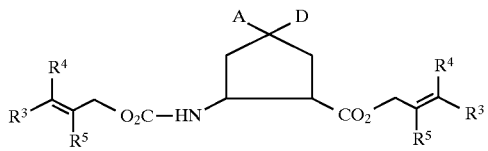

in which $R^3$, $R^4$, $R^5$, A and D have the abovementioned meanings, and finally the urethane and the ester function are split in inert solvents and in the presence of a Pd catalyst and/or a phosphine and a nucleophilic auxiliary.

2. Process according to claim 1, wherein the reaction of the dicarboxylic acid anhydride of the general formula (I) is carried out in a temperature range between –60° C.

3. Process according to claim 1, wherein the reaction of the dicarboxylic acid anhydride of the general formula (I) is carried out under a pressure in the range from 0.5 to 80 bar.

4. Process according to claim 1, wherein the Curtius rearrangement is carried out in a temperature range between 0° and +130° C.

5. Process according to claim 1, wherein the Curtius rearrangement is carried out under a pressure in the range from 0.5 to 5 bar.

6. Process according to claim 1, wherein, in the Curtius rearrangement, the base is employed in an amount of 1 to 3 mol per mole of the compound of the general formula (IVa).

7. Process according to claim 1, wherein the urethane and ester function are split off in a temperature range from 0° C.

8. Process according to claim 1, wherein the urethane and ester function are split off under a pressure in the range from 0.5 to 5 bar.

9. Enantiomerically pure compounds of the general formula (IV)

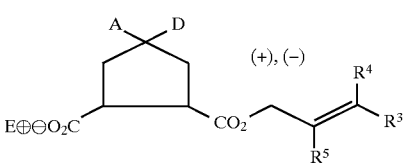

in which

A and D are identical or different and represent hydrogen, halogen or hydroxyl, or represent straight-chain or branched alkyl having up to 8 carbon atoms, which is optionally substituted once or twice in an identical or different manner by halogen, hydroxyl, phenyl, benzyloxy or carboxyl or by straight-chain or branched alkoxy, acyl or alkoxycarbonyl having in each case up to 6 carbon atoms or by a group of the formula $-NR^7R^8$, wherein $R^7$ and $R^8$ are identical or different and denote hydrogen, phenyl or straight-chain or branched alkyl having up to 6 carbon atoms, or A and D together represent a radical of the formula

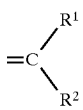

wherein $R^1$ and $R^2$ are identical or different and denote hydrogen, halogen or straight-chain or branched alkyl, alkoxy or hydroxyacyl having up to 8 carbon atoms, benzyl or phenyl, $R^3$, $R^4$ and $R^5$ are identical or different and represent hydrogen, or represent straight-chain or branched alkyl having up to 5 carbon atoms, or represent phenyl, which is optionally substituted up to 3 times in an identical or different manner by halogen, cyano, trifluoromethoxy, nitro or trifluoromethyl or by straight-chain or branched alkyl or alkoxy having in each case up to 6 carbon atoms, or $R^3$ represents a 5- to 7-membered aromatic heterocyclic radical having up to 3 heteroatoms from the series consisting of S, N and/or O, and E represents a chiral amine base, with the exception of monoallyl (–)-1,2-cis-4-methylene-cyclopentane-1,2-dicarboxylate, quinine salt.

10. Enantiomerically pure compounds of the general formula (IVa)

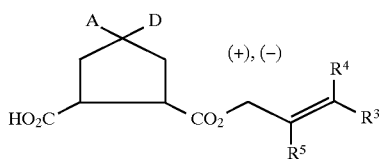

in which

A and D are identical or different and represent hydrogen, halogen or hydroxyl, or represent straight-chain or branched alkyl having up to 8 carbon atoms, which is optionally substituted once or twice in an identical or different manner by halogen, hydroxyl, phenyl, benzyloxy or carboxyl or by straight-chain or branched alkoxy, acyl or alkoxycarbonyl having in each case up to 6 carbon atoms or by a group of the formula —$NR^7R^8$, wherein $R^7$ and $R^8$ are identical or different and denote hydrogen, phenyl or straight-chain or branched alkyl having up to 6 carbon atoms, or A and D together represent a radical of the formula

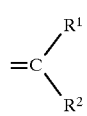

wherein $R^1$ and $R^2$ are identical or different and denote hydrogen, halogen or straight-chain or branched alkyl, alkoxy or hydroxyacyl having up to 8 carbon atoms, benzyl or phenyl, $R^3$, $R^4$ and $R^5$ are identical or different and represent hydrogen, or represent straight-chain or branched alkyl having up to 5 carbon atoms, or represent phenyl, which is optionally substituted up to 3 times in an identical or different manner by halogen, cyano, trifluoromethoxy, nitro or trifluoromethyl or by straight-chain or branched alkyl or alkoxy having in each case up to 6 carbon atoms, or $R^3$ represents a 5- to 7-membered aromatic heterocyclic radical having up to 3 heteroatoms from the series consisting of S, N and/or O, with the exception of monoallyl (−)-1,2-cis-4-methylene-cyclopentane-1,2-dicarboxylate, monoallyl (−)-1,2-cis-cyclopentane-1,2-dicarboxylate, and monophenylallyl (−)-1,2-cis-4-methylene-cyclopentane-1,2-dicarboxylate.

11. Enantiomerically pure compounds of the general formula (VII)

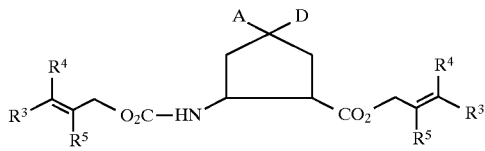

in which

A and D are identical or different and represent hydrogen, halogen or hydroxyl, or represent straight-chain or branched alkyl having up to 8 carbon atoms, which is optionally substituted once or twice in an identical or different manner by halogen, hydroxyl, phenyl, benzyloxy or carboxyl or by straight-chain or branched alkoxy, acyl or alkoxycarbonyl having in each case up to 6 carbon atoms or by a group of the formula —$NR^7R^8$, wherein $R^7$ and $R^8$ are identical or different and denote hydrogen, phenyl or straight-chain or branched alkyl having up to 6 carbon atoms, or A and D together represent a radical of the formula

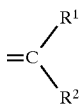

wherein $R^1$ and $R^2$ are identical or different and denote hydrogen, halogen or straight-chain or branched alkyl, alkoxy or hydroxyacyl having up to 8 carbon atoms, benzyl or phenyl, $R^3$, $R^4$ and $R^5$ are identical or different and represent hydrogen, or represent straight-chain or branched alkyl having up to 5 carbon atoms, or represent phenyl, which is optionally substituted up to 3 times in an identical or different manner by halogen, cyano, trifluoromethoxy, nitro or trifluoromethyl or by straight-chain or branched alkyl or alkoxy having in each case up to 6 carbon atoms, or $R^3$ represents a 5- to 7-membered aromatic heterocyclic radical having up to 3 heteroatoms from the series consisting of S, N and/or O.

12. Process according to claim 2, wherein the reaction of the dicarboxylic acid anhydride of the formula (I) is carried out in a temperature range between −20° C. and +25° C.

13. Process according to claim 3, wherein the reaction of the dicarboxylic acid anhydride of the formula (I) is carried out under normal pressure.

14. Process according to claim 4, wherein the Curtius rearrangement is carried out in a temperature range between 6° and 110° C.

15. Process according to claim 5, wherein the Curtius rearrangement is carried out under normal pressure.

16. Process according to claim 6, wherein in the Curtius rearrangement, the base is employed in an amount of 1 to 1.5 mol per mole of the compound of the general formula (IVa).

17. Process according to claim 7, wherein the urethane and ester function are split off in a temperature range from 20° C. to 80° C.

18. Process according to claim 8, wherein the urethane and ester function are split off under normal pressure.

* * * * *